US009340821B2

(12) United States Patent
Yang et al.

(10) Patent No.: US 9,340,821 B2
(45) Date of Patent: May 17, 2016

(54) SPECIFIC FLUORESCENT PROBE BASED ON ALBUMIN PSEUDO-ESTERASE HYDROLYSIS REACTION AND USE THEREOF

(71) Applicant: DALIAN INSTITUTE OF CHEMICAL PHYSICS, CHINESE ACADEMY OF SCIENCES, Dalian (CN)

(72) Inventors: Ling Yang, Dalian (CN); Jingnan Cui, Dalian (CN); Guangbo Ge, Dalian (CN); Zhaoming Liu, Dalian (CN); Lei Feng, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 14/787,868

(22) PCT Filed: Mar. 27, 2014

(86) PCT No.: PCT/CN2014/000334
§ 371 (c)(1),
(2) Date: Oct. 29, 2015

(87) PCT Pub. No.: WO2015/018177
PCT Pub. Date: Feb. 12, 2015

(65) Prior Publication Data
US 2016/0076076 A1    Mar. 17, 2016

(30) Foreign Application Priority Data
Aug. 6, 2013  (CN) .......................... 2013 1 0338267

(51) Int. Cl.
*C09B 57/08* (2006.01)
*C12Q 1/46* (2006.01)
*G01N 33/58* (2006.01)

(52) U.S. Cl.
CPC . *C12Q 1/46* (2013.01); *C09B 57/08* (2013.01); *G01N 33/582* (2013.01); *G01N 2333/765* (2013.01)

(58) Field of Classification Search
None
See application file for complete search history.

(56) References Cited

FOREIGN PATENT DOCUMENTS

CN         101942211 A    1/2011

OTHER PUBLICATIONS

Sun etc., "Synthesis and spectroscopic characterization of 4-butoxyethoxy-N-octadecyl-1,8-naphthalimide as a new fluorescent probe for the determination of proteins", Bioorganic & Medicinal Chemistry Letters 21 (2011) 3798-3804.
Song Wei etc., "4-alkoxyethoxy-N-octadecyl-1,8-naphthalimide fluorescent sensor for human serum albumin and other major blood proteins: design, synthesis and solvent effect", Luminescence 2013; 28: 318-326.
Chusen Huang,"Highly Selective Fluorescent Probe for Vicinal-Dithiol-Containing Proteins and in Situ Imaging in Living Cells", Angew. Chem. Int. Ed. 2011, 50, 7551-7556.
Mariya S. Liyasova, "Reaction of human albumin with aspirin in vitro: Mass spectrometric identification of acetylated lysines 199, 402, 519, and 545", Biochem Pharmacol 2010; 79 ,784-91.
Bin Li et al., "Butyrylcholinesterase, paraoxonase, and albumin esterase, but not carboxylesterase, are present in human plasma", Biochem Pharmacol. Nov. 25, 2005;70(11) 1673-84.
Basil T. Doumas et al., "Origins of Dye-Binding Methods for Measuring Serum Albumin", Clin Chem., 2009, 55, 583.
Guang-Bo Ge, "The role of serum albumin in the metabolism of Boc5: Molecular identification, species differences and contribution to plasma metabolism," Eur. J. Pharm. Sci. 2013; 48,360-9.
Oksana Lockridge "Pseudo-esterase Activity of Human Albumin Slow Turnover on Tyrosine 411 and Stable Acetylation of 82 Residues Including 59 Lysines", J Biol Chem 2008; 283 ,33,22582-90.
Ellen G. Duysen et al., "Increased Hepatotoxicity and Cardiac Fibrosis in Cocaine-Treated Butyrylcholinesterase Knockout Mice", J Clin Pathol. 2003, 56, 780.
Oksana Lockridge, "Mass spectrometry to identify new biomarkers of nerve agent exposure" reported in Apr. 2010, available online such as http://oai.dtic.mil/oai/oai?verb=getRecord&metadataPrefix=html&identifier=ADA539367 (confirmed on Oct. 29, 2015).

*Primary Examiner* — Suzanne M Noakes
*Assistant Examiner* — Stephen Chong
(74) *Attorney, Agent, or Firm* — Enshan Hong; VLP Law Group LLP

(57) ABSTRACT

A pseudo-esterase activity-based fluorescent probe for specific detection of albumin, which has a carboxylic ester bond that can be selectively cleaved by human serum albumin (HSA), therefore forming a hydrolysate, which has a fluorescence emission spectrum significantly different from that of the fluorescent probe. According to the fluorescence intensity of the fluorescent probe and hydrolysate, we can detect the content of HSA in a biological sample.

5 Claims, 3 Drawing Sheets

SPECIFIC FLUORESCENT PROBE BASED ON ALBUMIN PSEUDO-ESTERASE HYDROLYSIS REACTION AND USE THEREOF

PRIORITY CLAIM

This is a U.S. national stage of application No. PCT/CN2014/00334 filed on Mar. 27, 2014, which claims priority from China Patent Application No. 201310338267.7 filed Aug. 6, 2013, the entire content of which is incorporated herein as reference.

FIELD OF THE INVENTION

The present invention belongs to the medical technology, including a pseudo-esterase activity-based fluorescent probe for specific detection of albumin and its applications.

BACKGROUND OF THE INVENTION

Human serum albumin (HSA), the most abundant, versatile and complex protein in human blood, account for 50-60% of the total protein in plasma. See *Biochem Pharmacol.* 2005 Nov. 25; 70(11): 1673-84. In human body, HSA makes a large contribution to plasma colloid osmotic pressure, mediates coagulation, helps to maintain normal microvascular permeability, and serves as a carrier protein for fatty acids, cholochrome, amino acid, steroid hormone, metal ions, and drug molecules. In human serum, the normal albumin range is 34-54 g/L. See Nlm.nih.gov. Retrieved 2010 May 12. But many diseases, including liver complaint (cirrhosis especially), nephrotic syndrome, tumors, protein-losing enteropathy, empyrosis, malnutrition and so on, will cause a decline in the level of serum albumin, while a high-protein diet and chronic dehydration will raise the HSA levels. So it has been clinically used for disease diagnosis to quantitatively determine the albumin levels in human blood. It will be necessary to give patients HSA by injection, when the HSA level is much lower than the normal level. It has been confirmed by a large number of clinical practices that monitoring the HSA level will be reference for the early diagnosis of liver or kidney disease, and diseases after operation. More importantly, urinary microalbumin has been widely used as an important biomarker for patients with renal damage (like diabetes, hypertension and poststreptococcal acute glomerulonephritis), endothelial dysfunction, cardiac disease and venous thromboembolism. The normal range of the renal small albumin in human is shown in Table 1.

TABLE 1

The diagnostic value of the microalbuminuria

| | Gender | Lower limit | Upper limit | Unit |
|---|---|---|---|---|
| 24 hours urine | | 30 | 300 | mg/24 h |
| short haul urine | | 20 | 200 | µg/min |
| single-point urine | | 30 | 300 | mg/L or µg/g |
| single-point urine/ Urinary C-peptide Creatinine Ratio | Female | 3.5 | 25 or 35 | mg/mmol |
| | | 30 | 400 | µg/mg |
| | Male | 2.5 or 3.5 | 25 or 35 | mg/mmol |
| | | 30 | 300 | µg/mg |

At present there are kinds of methods for HA quantification, including electrophoresis, immunoassay methods, as well as dye-binding procedures. Wherein the electrophoresis method is time-consuming with low specificity and it is easy to overestimate the HSA concentrations. See Clinical Chemistry: Theory, Analysis, Correlation, Mosby, 5th edition, 2009. While immunoassay is a specific method for HSA quantification, but it is high-cost, so it is less used in clinical application. Although the application of dye-binding method is relatively wide, its specificity is unable to be guarantee, for the reason that this method is based on the conjugation of dye molecule and parts of HSA or modifying the function of individual amino acids, but other tissue proteins in body also have the ability to bind these dyes. Bromcresol green (BCG) and bromcresol purple are widely used to quantitative detect albumin in clinic on account of simplicity, cheap and relatively higher specificity. But due to its low sensitivity (see Clinical Chemistry: Theory, Analysis, Correlation, Mosby, 5th edition, 2009.), hard to ensure the quantitative accuracy, overvalued (See *J Clin Pathol.* 2003, 56, 780.) or underestimated (See *Clin Chim Acta.* 1986, 155, 83.) often appear, and dye-binding-based assays can be interfered by the nonspecific interference from biological samples (See *Clin Chem.*, 2009, 55, 583). Therefore, it is necessary to develop an easy-operating, highly specific, accurate faithful quantitative method for HSA quantification.

In recent years, domestic and overseas scholars found that HSA has catalytic properties and participates in catalyzing the hydrolysis of various molecules with ester bond in structure (Biochem Pharmacol 2010; 79 (5):784-91 & J Biol Chem 2008; 283 (33):22582-90), after a specific cleavage of the carboxylic ester bond, the phenylbenzoate group covalently bound to the residues of HSA accompanying with releasing the hydrolysate that contains free phenolic hydroxyl group. Guangbo Ge et al. also found that some small molecules with ester bond in structure can be catalyzed by HSA, for examples, Boc5, receptor agonist of GLP-1, can only be catalyzed by albumin in vivo, while other human esterase don't participate in the hydrolysis of this compound (*Eur. J. Pharm. Sci.* 2013; 48: 360-9). Recent domestic and overseas researches suggest that we can design and develop pseudo-esterase activity-based specific fluorescent probes for activity evaluation and quantification of HSA. The present invention provides the applications of a specific fluorescent probe to HSA, it is a dibenzoyl ester derivative, which replaced the C4 hydroxyl of N-n-butyl-4-hydroxy-1,8-naphthalimide, the fluorescence emission spectrum of the pseudo-esterase activity-based hydrolysis product is significantly different from that of the substrate molecule. This hydrolysis reaction has the characteristics of high selectivity, metabolic product easy to detect.

SUMMARY OF THE INVENTION

The purpose of the present invention is to provide a specific fluorescent probe, which is a dibenzoyl ester derivative, and its applications; this probe is used to detect albumin levels in human serum, plasma, or urine by testing the fluorescence intensity of samples, there are obvious differences between the fluorescence emission wavelength of the prototype and hydrolysate, and the product is more likely to detect.

The present invention provides a pseudo-esterase activity-based fluorescent probe. Wherein the carboxylic ester bond of the probe could be selectively cleaved by human serum albumin (HSA) to release a fluorescent product of which the fluorescence emission spectrum is significantly different from that of the substrate molecule, according to the content of substrate and product we can deduce the content and function of HSA in the system. This specific fluorescent probe is a dibenzoyl ester derivative, which replaced the C4 hydroxyl of N-n-butyl-4-hydroxy-1,8-naphthalimide, the structural general formula are shown in Scheme (1), wherein $R_1$ is —H, —CH₃, —OCH₃, —OC₂H₅, and R₂ is C2-C8 alkyl, C2-C8 halogenated alkyl group or any of its derivatives.

Scheme 1

The present invention also provides the applications of a kind of specific fluorescent probe for quantitative determination of HSA levels in different samples, wherein the compound as shown in scheme 1 was used as a specific substrate of hydrolysis metabolism for HSA, human serum albumin levels in different samples (including recombinant albumin, single enzyme, tissue preparation liquid, all kinds of tissue cells and other biological systems) were detected by the quantitative detection of the elimination of substrate and the generation of hydrolysis products in unit time. Specific method is:

This specific fluorescent probe is a dibenzoyl ester derivative, which replaced the C4 hydroxyl of N-n-butyl-4-hydroxy-1,8-naphthalimide, the concentrations of the probe substrate are between ⅒ and 10 Km, Km is chosen as the optimal concentration of substrate when determination at a single point (Km is Mie kinetic constant).

The system is phosphate buffer, reaction temperature is between 20 to 60° C. (The optimum reaction temperature is 37° C.) and pH value of the incubation system is between 5.5 and 10.5 (The optimum pH value is 7.4)

The reaction time is 5-120 minutes to ensure that the hydrolysate amount corresponding to the substrate described above achieve the limit of quantification.

HSA activity levels in different samples are detected with the quantitative detection of the elimination of substrate and the generation of hydrolysis products in unit time as the evaluating index.

The present invention provides applications of a kind of specific fluorescent probe for the quantitative determination of HSA levels in different samples, wherein both the probe substrate and its hydrolysate possess fluorescent properties, the rapid and sensitive determination for substrate and product can be realized by using fluorescence detector, fluorescence detection conditions: excitation wavelength is between 300 and 500 nm, emission wavelength is between 410 and 600 nm.

The present invention provides applications of a kind of specific fluorescent probe for the quantitative determination of human serum albumin levels in different samples, wherein the samples described above are human serum, plasma and urine.

Recombinant expression of HSA incubation system were investigated, through specific inhibition experiment, single enzymes metabolic reactions, and the kinetics of enzyme reaction, and it was proved that dibenzoyl ester derivatives, which replaced the C4 hydroxyl of N-n-butyl-4-hydroxy-1,8-naphthalimide, could be selectively cleaved by HSA to release hydrolysate, that is C4 ester bond rupture of probe. (as shown in FIG. 4)

Using the albumin-specificity probe for the detection of albumin described in the present invention, has the following outstanding advantages:

(1) High specificity: dibenzoyl ester derivatives, which replaced the C4 hydroxyl of N-n-but yl-4-hydroxy-1,8-naphthalimide could be selectively cleaved by HSA to release hydrolysate, that is C4 ester bond rupture of probe.

(2) Cheap and available: dibenzoyl ester derivatives, which replaced the C4 hydroxyl of N-n-butyl-4-hydroxy-1,8-naphthalimide and their hydrolysis products can all be obtained by chemical synthesis, and the synthesis process is simple.

(3) High sensitivity: derivatives of N-n-butyl-4-hydroxy-1,8-naphthalimide have good features in fluorescence emission spectrum (410-600 nm), the substrate and its hydrolysis metabolites have different fluorescence emission spectrum characteristics, which makes it easy to do a distinguish detection, at the same time, standard curve drawing can be approved by the ratio method for quantitative determination.

DETAILED DESCRIPTION OF THE INVENTION

The following example will further explain the invention, but not limit the present invention.

EXAMPLE 1

Synthesis of
N-n-butyl-1,8-naphthalimide-4-phenylbenzoate
(Fluorescent Probe A)

(1) To a solution of 4-hydroxy-N-butyl-1,8-naphthalimide (0.5 mmol) and Et₃N (0.625 mmol) in 10 mL of THF, dibenzoyl chloride (0.6 mmol, mixed with 10 mL of CH₂Cl₂) was added dropwise at 0° C.

(2) After stirring at this temperature for 1 h, the mixture was warmed to room temperature and stirred overnight.

(3) The solvent was removed in vacuo, and the residual solid was purified by chromatography (silica gel, EtOAc—hexane as eluent, 1:3, v/v) to afford 113 mg of A as a white solid.

Figure 1:
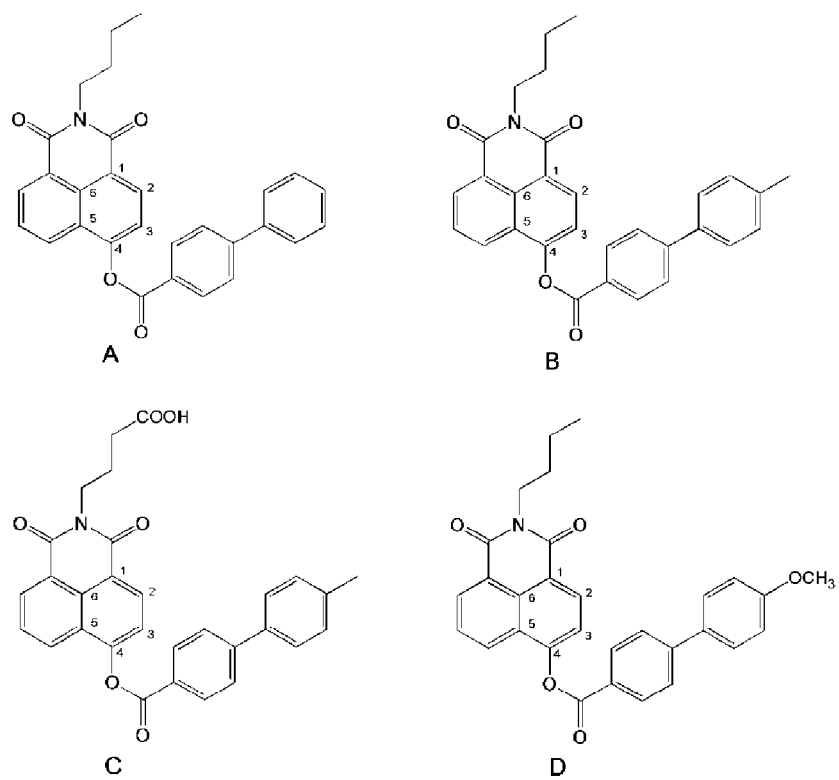
FIG. 1. Structure of dibenzoyl ester derivatives, which replaced the C4 hydroxyl of N-n-butyl-4-hydroxy-1,8-naphthalimide; and A is fluorescent probe A, B is fluorescent probe B, C is fluorescent probe C, D is fluorescent probe D.
Figure 2:
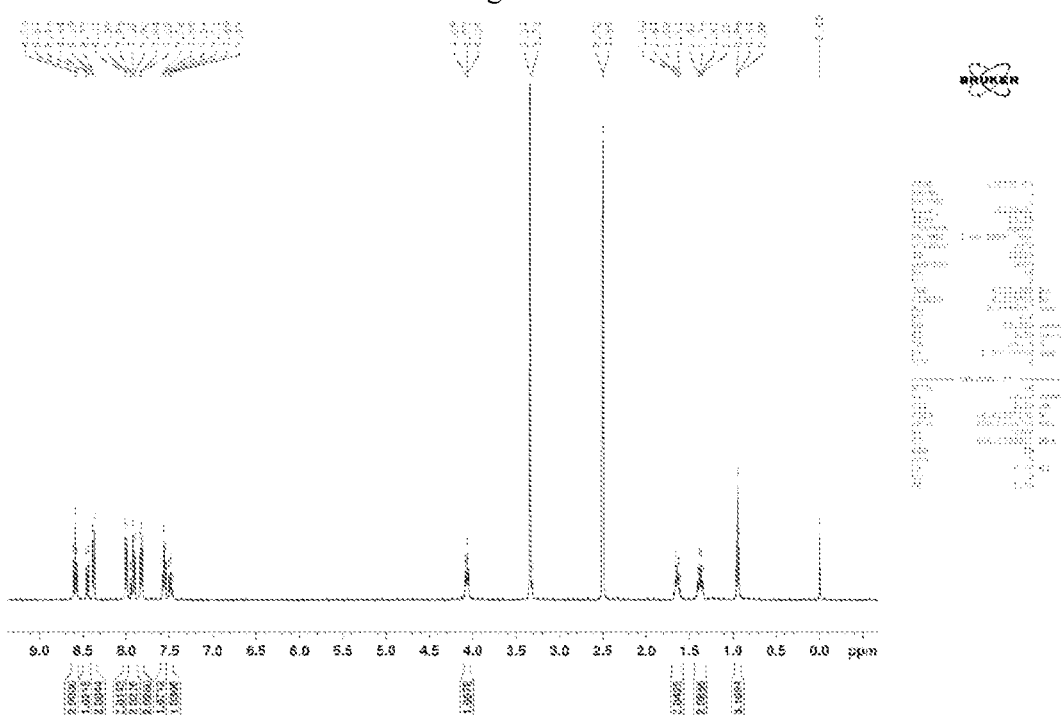
FIG. 2. 1H-NMR of N-n-butyl-1,8-naphthalimide-4-phenylbenzoate.
Figure 3:
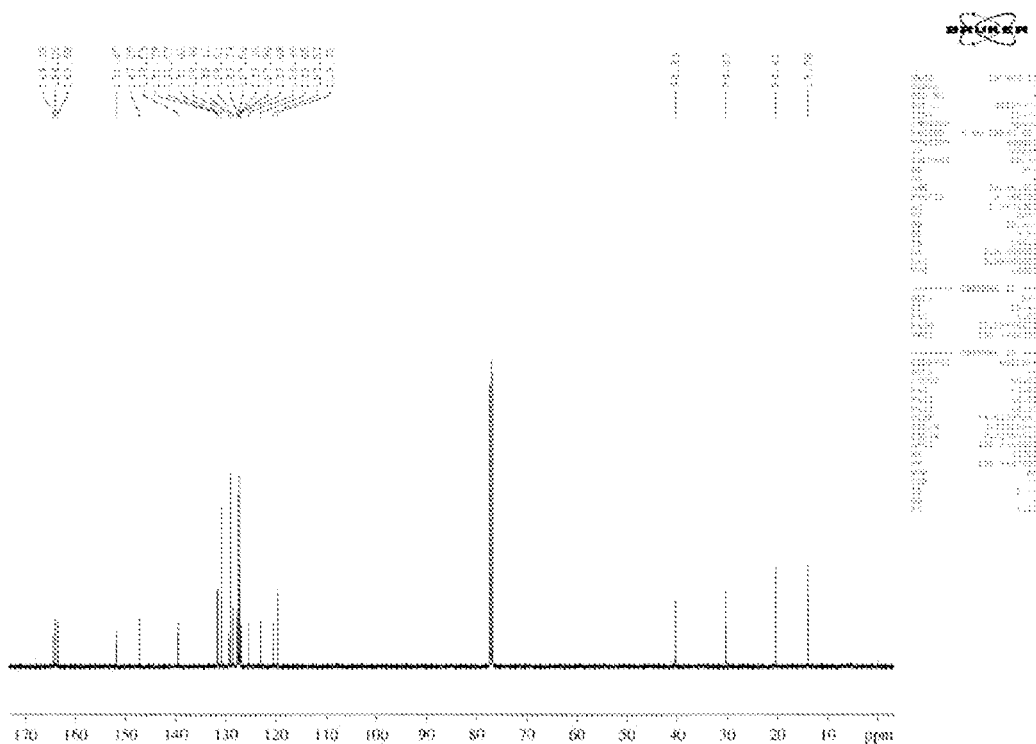
FIG. 3. 13C-NMR of N-n-butyl-1,8-naphthalimide-4-phenylbenzoate.

(4) Then validating the white solid A compound structure, its $^1$H NMR and $^{13}$C NMR are shown in FIG. 2 and FIG. 3.

EXAMPLE 2

Synthesis of N-n-butyl-1,8-naphthalimide-4-(4-methylphenylbenzoate) (Probe B)

(1) To a solution of 4-hydroxy-N-butyl-1,8-naphthalimide (0.5 mmol) and Et$_3$N (0.625 mmol) in 10 mL of THF, 4-methyl-dibenzoyl chloride (0.6 mmol, mixed with 10 mL of CH$_2$Cl$_2$) was added dropwise at 0° C.

(2) After stirring at this temperature for 1 h, the mixture was warmed to room temperature and stirred overnight.

(3) The solvent was removed in vacuo, and the residual solid was purified by chromatography (silica gel, EtOAc—hexane as eluent, 1:3, v/v) to afford 241 mg of B as a white solid.

EXAMPLE 3

Synthesis of N-3-carboxy propyl-1,8-naphthalimide-4-phenylbenzoate (Probe C)

(1) To a solution of 4-hydroxy-N-3-carboxy propyl-1,8-naphthalimide (0.5 mmol) and Et$_3$N (0.625 mmol) in 10 mL of THF, dibenzoyl chloride (0.6 mmol, mixed with 10 mL of CH$_2$Cl$_2$) was added dropwise at 0° C.

(2) After stirring at this temperature for 1 h, the mixture was warmed to room temperature and stirred overnight.

(3) The solvent was removed in vacuo, and the residual solid was purified by chromatography (silica gel, EtOAc—hexane as eluent, 1:3, v/v) to afford 95 mg of C as a white solid.

EXAMPLE 4

Synthesis of N-n-butyl-1,8-naphthalimide-4-(4-methoxyphenylbenzoate) (Probe D)

(1) To a solution of 4-hydroxy-N-butyl-1,8-naphthalimide (0.5 mmol) and Et$_3$N (0.625 mmol) in 10 mL of THF, 4-methoxy-dibenzoyl chloride (0.6 mmol, mixed with 10 mL of CH$_2$Cl$_2$) was added dropwise at 0° C.

(2) After stirring at this temperature for 1 h, the mixture was warmed to room temperature and stirred overnight.

(3) The solvent was removed in vacuo, and the residual solid was purified by chromatography (silica gel, EtOAc—hexane as eluent, 1:3, v/v) to afford 143 mg of D as a white solid.

EXAMPLE 5

Hydrolysis Selectivity of Fluorescent Probe A (1) 196 μL PBS (pH=6.0, 10 mM) containing CES1b, CES1c. CES2 (5 μg/mL), acetylcholin esterase (0.1 U/L), butyrylcholine esterase (20 U/L), plasma (1%), HSA (0.5 mg/mL). BSA (0.5 mg/mL) was preincubated with stirring for 10 min at 37° C.

(2) 4 μL fluorescent probe A (0.5 mM) was added to the above solution to make the final concentration of the fluorescent probe to 10 μM in the test sample, then incubated with stirring at 37° C.

(3) 30 min later, 200 μL ice-cold CH$_3$CN was added to the sample and stirred, then the reaction was stopped.

Figure 4:
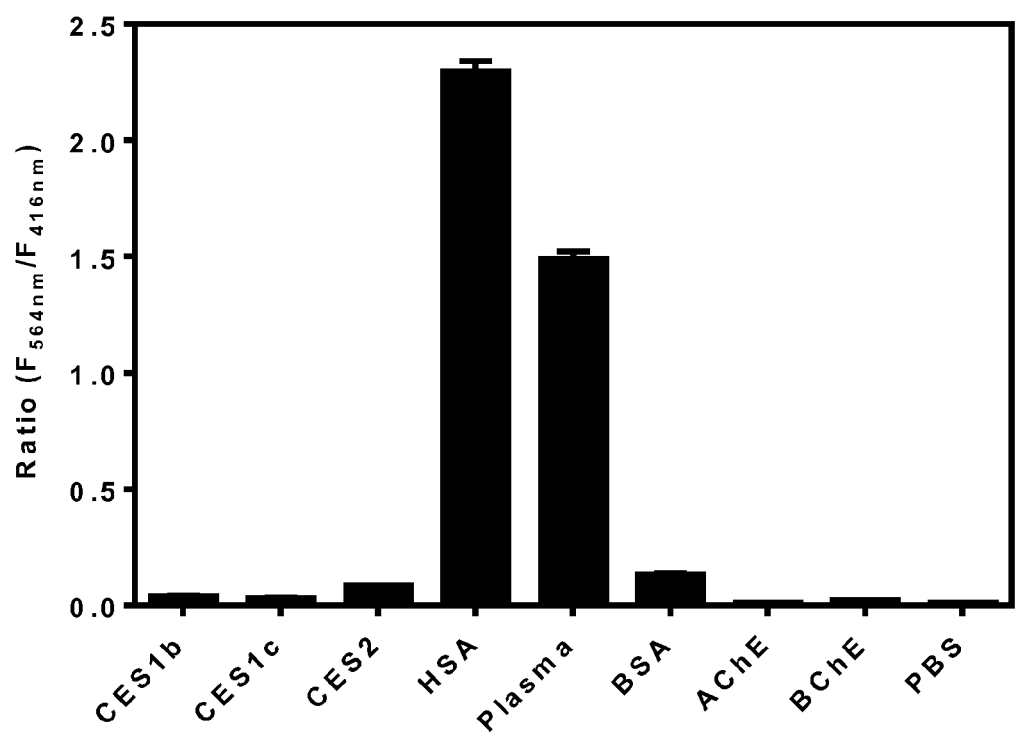
FIG. 4. Restructuring single enzyme screening test results of N-n-butyl-1,8-naphthalimide-4-phenylbenzoate's derivatives.
Figure 5:
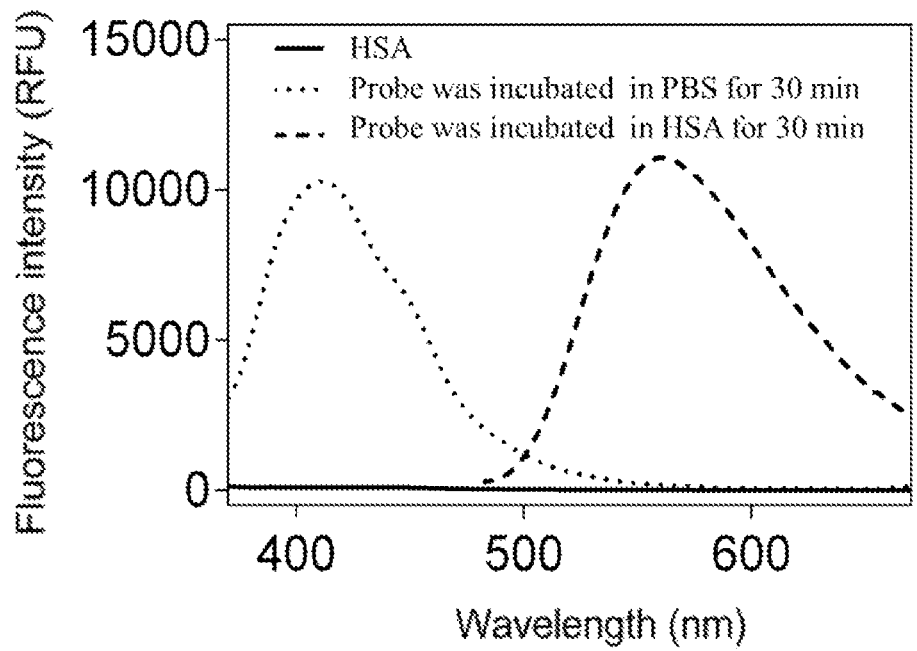
FIG. 5. Fluorescence emission spectra of N-n-butyl-1,8-naphthalimide-4-phenylbenzoate and its hydrolysate ($\lambda ex=342/452$ nm).

(4) Detecting the fluorescence intensity of probe A ($\lambda$ex=342 nm, $\lambda$em=416 nm) and hydrolysate A1 ($\lambda$ex=452 nm, $\lambda$em=564 nm) at corresponding wave length and calculating the fluorescence intensity ratio of A1 to A. (As can be seen in FIG. 4 and FIG. 5).

EXAMPLE 6

Quantitative Working Curve of HSA (1) 5 mg/mL of human serum albumin (HSA) standard solution was diluted by PBS to obtain a series of working solution with different concentrations (0, 10, 20, 50, 100, 200, 300, 400, 500, 600, 700, 800, 900, 1000 mg/L) (Table 2), then samples were incubated at 37° C. for 10 min.

(2) Adding 20 μL fluorescent probe B (0.5 mM) to each sample (980 μL) to make the final concentration of the fluorescent probe to 0.5 mM, then samples were incubated turmoil at 37° C. for 30 min, 1 mL ice-cold CH$_3$CN was added and stirred for 15 second, then the reaction was stopped.

TABLE 2

Preparation of a series of working solution of HSA

| NO | Volume of HSA | The volume of the diluent | Final concentration of HSA |
|---|---|---|---|
| 0 | 200 μL | 780 μL | 1000 mg/L |
| 1 | 180 μL | 800 μL | 900 mg/L |
| 2 | 160 μL | 820 μL | 800 mg/L |
| 3 | 140 μL | 840 μL | 700 mg/L |
| 4 | 120 μL | 860 μL | 600 mg/L |
| 5 | 100 μL | 880 μL | 500 mg/L |
| 6 | 80 μL | 900 μL | 400 mg/L |
| 7 | 60 μL | 920 μL | 300 mg/L |
| 8 | 40 μL | 940 μL | 200 mg/L |
| 9 | 20 μL | 960 μL | 100 mg/L |
| 10 | Absorbing 100 μL from 0 tube | 880 μL | 50 mg/L |
| 11 | Absorbing 40 μL from 0 tube | 940 μL | 20 mg/L |
| 12 | Absorbing 20 μL from 0 tube | 960 μL | 10 mg/L |
| 13 | 0 μL | 980 μL | 0 mg/L |

Figure 6:
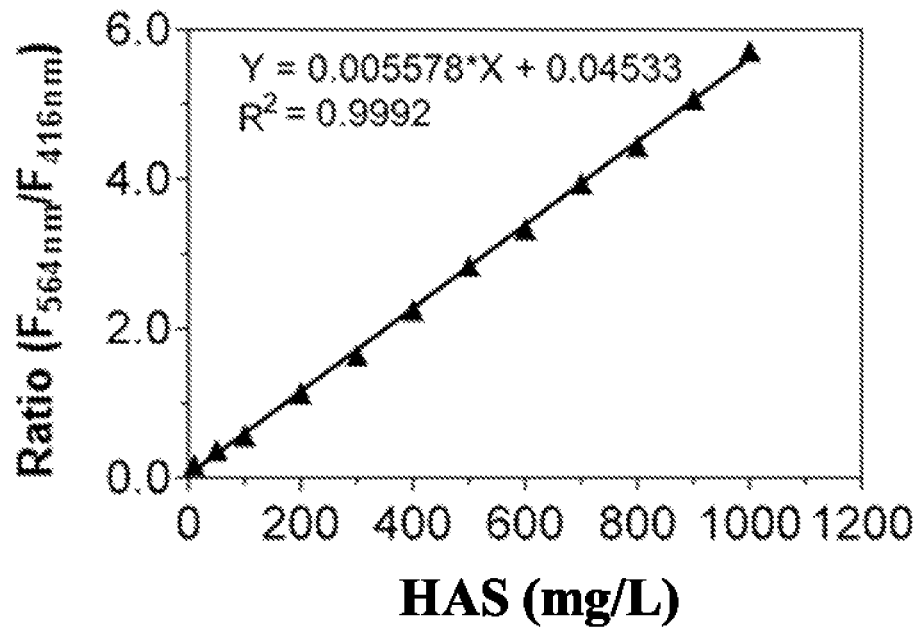
FIG. 6. Fitting curve of the generation of dibenzoyl ester hydrolysate against HSA concentrations.

(3) Detecting the fluorescence intensity of probe B ($\lambda_{ex}$=342 nm, $\lambda_{em}$=416 nm) and hydrolysate B1 ($\lambda_{ex}$=452 nm, $\lambda_{em}$=564 nm) at corresponding wave length, the working curves (fluorescence intensity ratio of B1 to B versus the concentration of HSA) were fitted, curve equation is Y=0.005578×X+0.04533 ($R^2$=0.9992) (As can be seen in FIG. 6).

EXAMPLE 7

Quantitative Analysis of Albumin in Human Plasma Sample (1) 1 μL of human plasma sample was diluted to 200 times by PBS (pH 7.4, 10 mM), then samples were incubated turmoil at 45° C. for 10 min.

(2) 4 μL fluorescent probe B (0.5 mM) was added to the above solution to make the final concentration of the fluorescent probe to 10 μM, and then samples were incubated at 45° C.

(3) After 30 min, 200 μL of ice-cold CH$_3$CN was added to the sample and stirred, and then the reaction was stopped.

(4) Detecting the fluorescence intensity of probe B ($\lambda_{ex}$=342 nm, $\lambda_{em}$=416 nm) and hydrolysate B1 ($\lambda_{ex}$=452 nm, $\lambda_{em}$=564 nm) at corresponding wavelength and calculating the fluorescence intensity ratio of B1 to B, the fluorescence ratio was substituted into working curve from example 2, concentration of HSA in plasma albumin was calculated as 46.2 mg/L.

EXAMPLE 8

Quantitative Analysis of Albumin in Urine Sample (1) 490 μL of human urine sample was diluted by 490 μL PBS (pH 7.4, 10 mM), and then samples were incubated at 45° C. for 10 min.

(2) 20 μL fluorescent probe C (0.5 mM) was added to the above solution to make the final concentration of the fluorescent probe to 10 μM, and then samples were incubated turmoil at 37° C. for 30 min, 1 mL ice-cold $CH_3CN$ was added to the sample and stirred for 15 second, then the reaction was stopped.

(3) Detecting the fluorescence intensity of probe C ($\lambda_{ex}$=342 nm, $\lambda_{em}$=416 nm) and hydrolysate C1 ($\lambda_{ex}$=452 nm, $\lambda_{em}$=564 nm) at corresponding wavelength and the fluorescence intensity ratio of C1 to C was calculated.

(4) Finding the corresponding albumin level in the working curve, concentration of HSA in the sample was calculated as 48 mg/L.

EXAMPLE 9

Quantitative Analysis of HSA in Recombinant Expression System (1) 10 mg recombinant HSA was weighted and dissolved in PBS (pH=7.4), configuring to 1 mg/mL albumin solution at 37° C.

(2) 20 μL fluorescent probe D (0.5 mM) was added to the above solution to make the final concentration of the fluorescent probe to 10 μM, and then samples were incubated turmoil at 37° C. for 30 min, 1 mL ice-cold $CH_3CN$ was added to the sample and stirred for 15 second, then the reaction stopped.

(3) Detecting the fluorescence intensity of probe D ($\lambda_{ex}$=342 nm, $\lambda_{em}$=416 nm) and hydrolysate D1 ($\lambda_{ex}$=452 nm, $\lambda_{em}$=564 nm) at corresponding wavelength and the fluorescence intensity ratio of D1 to D was calculated.

(4) Based on the working curve, the concentration of HSA in this sample (1 mg/mL recombinant HSA solution) was calculated as 14.9 μM.

We claim:

1. A fluorescent probe of formula (I):

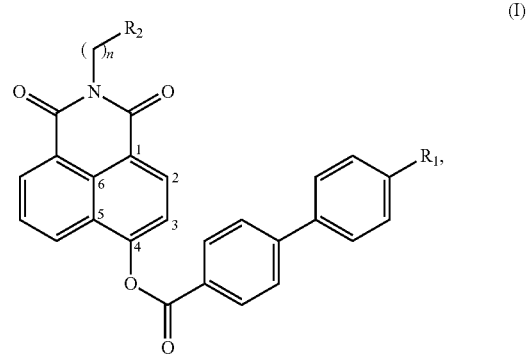

wherein $R_1$ is selected from the group consisting of —H, —$CH_3$, —$OCH_3$, —$OC_2H_5$, and $R_2$ is selected from the group consisting of C2-C8 alkyl, halogenated alkyl, and its derivatives.

2. A method of quantitatively determining the amount of human serum albumin (HSA) in a sample comprising:
    subjecting the fluorescent probe of claim 1, which has a carboxylic ester bond, to a hydrolysis reaction in the presence of the HSA so that the carboxylic ester bond is selectively cleaved, the amount of the fluorescent probe is reduced, and/or a hydrolysate is formed;
    detecting the reduced amount of the fluorescent probe and/or formed amount of the hydrolysate in a unit time; and
    determining the amount of the HSA in the sample based on the reduced amount of the fluorescent probe and/or formed amount of the hydrolysate in the unit time.

3. The method of claim 2 wherein the sample is selected from the group consisting of recombinant albumin, human tissue preparation liquid, and various types of tissue cells.

4. The method of claim 2 wherein the hydrolysis reaction is carried out in phosphate buffer under conditions as follows: the concentration of the fluorescent probe is between 1/10 and 10 Km; the pH value of an incubation system is between 5.5 and 10.5; and the temperature of the hydrolysis is between 20 to 60° C.

5. The method of claim 2 wherein both the fluorescent probe and the hydrolysate have a fluorescent property which enables effective detection of the fluorescent probe and the hydrolysate via a fluorescence detector under conditions as follows: excitation wavelength of between 300 and 500 nm, and emission wavelength of between 410 and 600 nm.

* * * * *